United States Patent [19]

Lewis

[11] Patent Number: 4,645,849

[45] Date of Patent: Feb. 24, 1987

[54] HYDROGENATION OF UNSATURATED HYDROCARBONS WITH CYCLOMETALLATED TRANSITION METAL CATALYSTS

[75] Inventor: Larry N. Lewis, Scotia, N.Y.

[73] Assignee: General Electric Company, Schenectady, N.Y.

[21] Appl. No.: 693,412

[22] Filed: Jan. 22, 1985

[51] Int. Cl.$^4$ .................. C07F 15/00; C07F 7/08; C07C 5/05; C07C 5/02

[52] U.S. Cl. .................... 556/16; 556/450; 556/453; 556/466; 556/467; 585/266; 585/273; 585/274; 585/275; 585/276

[58] Field of Search .............. 556/16, 450, 453, 466, 556/467; 585/266, 275, 276, 273, 274

[56] References Cited

U.S. PATENT DOCUMENTS

| | | | |
|---|---|---|---|
| 3,597,461 | 8/1971 | L'Eplattenier et al. | 556/16 |
| 3,647,832 | 3/1972 | Chabardes et al. | 556/16 X |
| 3,729,512 | 4/1973 | L'Eplattenier et al. | 556/16 X |
| 3,793,355 | 2/1974 | Wilkinson | 556/16 X |
| 3,849,480 | 11/1974 | Knowles et al. | 585/275 X |
| 3,939,219 | 2/1976 | Wilkinson | 585/275 |
| 4,012,399 | 3/1977 | Hechenbleikner et al. | 556/16 X |
| 4,151,114 | 4/1979 | Oswald et al. | 585/275 X |
| 4,268,454 | 5/1981 | Pez et al. | 585/275 X |
| 4,323,698 | 4/1982 | Haag et al. | 585/276 X |
| 4,578,496 | 3/1986 | Panster et al. | 556/467 UX |

OTHER PUBLICATIONS

J. Dehand and M. Pfeffer, "Cyclometallated Compounds", *Coordination Chemistry Reviews*, 18 (1976) 327-352.

Michael I. Bruce, "Cyclometalation Reactions", *Angew. Chem. Int. Ed. Eng.*, 16 (1977) 73-86.

*Primary Examiner*—Paul F. Shaver
*Attorney, Agent, or Firm*—James Magee, Jr.; James C. Davis, Jr.

[57] ABSTRACT

A method for hydrogenating olefins and alkynes is provided wherein the unsaturated hydrocarbon is reacted under mild conditions in the presence of a cyclometallated transition metal catalyst which shows greater resistance to degradation caused by oxidation.

14 Claims, No Drawings

HYDROGENATION OF UNSATURATED HYDROCARBONS WITH CYCLOMETALLATED TRANSITION METAL CATALYSTS

BACKGROUND OF THE INVENTION

This invention relates to the hydrogenation of unsaturated groups in the presence of transition metal catalysts. More particularly, this invention relates to the reaction of hydrogen with unsaturated hydrocarbons in the presence of a transition metal catalyst containing a cyclometallated group to provide the corresponding saturated hydrocarbon. The use of transition metal catalysts for olefin hydrogenation is well-known in the art as indicated by Kirk-Othmer in *Encyclopedia of Chemical Technology*, 6, (1978), pp. 583-584. James discusses a series of transition metal catalysts within *Advancements in Organometallic Chemistry*, 17 (1979) 319. In addition, Kirk-Othmer describes transition metal catalyst suitable for hydrogenation in the *Encyclopedia of Chemical Technology* (1978) at volume 6, p. 793 and volume 4, p. 842, which include nickel, cobalt, platinum, palladium, chromium, zinc, rhodium and molybdenum. Complexes of these transition metals are utilized to provide catalysis of the hydrogenation reaction within a homogeneous system. Many of these transition metal complexes are sensitive to moisture and air and lose their activity in the homogeneous system very quickly. It is desirable to obtain a transition metal complex which exhibits greater stability within the reaction medium and is less susceptible to oxidation in the presence of air and moisture.

Cyclometallated transition metal complexes have been described by Dehand and Pfeffer in *Coordination Chemistry Reviews*, 18 (1976) 327-352 and Michael Bruce, in *Angew. Chem. Int. Ed. Eng.*, 16 (1977) 73-86, which are incorporated herein by reference. These references discuss various species of cyclometallated complexes, their syntheses, their physical properties and some chemical reactions of the ring structures of the cyclometallated complexes. The use of the cyclometallated complexes as hydrogenation catalysts has heretofore never been suggested. The cyclometallated complexes have never been employed in a catalytic system.

SUMMARY OF THE INVENTION

This invention provides a method for hydrogenating unsaturated hydrocarbons which comprises reacting an unsaturated hydrocarbon with hydrogen in a solution of cyclometallated complex catalyst at a temperature above about 20° C., said unsaturated hydrocarbon comprising less than about 50 mole percent of the reaction mixture and being selected from the group consisting of aliphatic and cyclic olefins and alkynes of from 2 to 10 carbon atoms, aromatic hydrocarbons of from 8 to 18 carbon atoms having olefinic or alkyne functionality within hydrocarbon radicals of from 2 to 4 carbon atoms and siloxanes of from 1 to 10 —(Si—O)— units having olefinic or alkyne functionality within hydrocarbon radicals of from 2 to 4 carbon atoms, subject to the proviso that said unsaturated hydrocarbons contain no acidic functional groups, and said cyclometallated complex catalysts having a 4–6 membered ring with a chemically combined unit of the formula

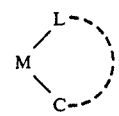

wherein M is a transition metal, L is a ligand selected from the group consisting of phosphorus, nitrogen, arsenic, oxygen and sulfur and C is a covalently bonded carbon atom of a hydrocarbon species having at least 6 carbon atoms.

OBJECTS OF THE INVENTION

An object of the present invention is to provide a catalyst for the hydrogenation of olefins and alkynes with reduced sensitivity to moisture and air.

Another object of the present invention is to provide a homogeneous transition metal catalyst for the hydrogenation of olefins and alkynes which exhibits a longer lifetime than the hydrogenation catalysts previously utilized.

Another object of the present invention is to provide a hydroganation catalyst which can be regenerated by the addition of starting materials and the use of higher temperatures.

A further object of the present invention is to provide a cyclometallated transition metal complex catalyst which provides high conversion rates for the hydrogenation of olefins and alkynes.

STATEMENT OF THE INVENTION

The essential feature of the process comprising this invention is the use of cyclometallated transition metal complexes as catalysts. The terms "cyclometallated transition metal complex" and "cyclometallated complex", as used herein, refer to transition metal complexes which contain a ring system having a chemically combined unit of the formula $$\begin{array}{c} L\text{-} \\ / \quad \backslash \\ M \quad ) \quad \quad I \\ \backslash \quad / \\ C\text{--} \end{array}$$

wherein L is a ligand selected from the group consisting of phosphorus, nitrogen, arsenic, oxygen and sulfur atoms, M is a transition metal and C is a covalently bonded carbon atom. A bond lies between the transition metal "M" and the ligand "L". A covalent bond lies between the transition metal and the carbon atom. The ligand "L" and carbon atom "C" are linked to provide a 4–6 membered ring structure with the transition metal. The carbon atom and ligand "L" are typically a part of one coordination complex that appears on the transition metal. The carbon atom is part of a hydrocarbon species having at least 6 carbon atoms, which is preferably an aromatic hydrocarbon and the ligand "L" is then bonded either directly or indirectly to this hydrocarbon species as part of a coordination complex.

The transition metals are preferably selected from the group consisting of ruthenium, palladium, platinum, nickel, cobalt, rhodium, and manganese. The transition metal which is most preferred typically depends on the type of olefin which is hydrogenated. For the hydrogenation of unsaturated aliphatic hydrocarbons, ruthenium, palladium and cobalt are the most preferred transition metals.

Suitable cyclometallated transition metal complexes and cyclometallated ring structures are described in J. Dehand and M. Pfeffer in "Cyclometallated Compounds", *Coordination Chemistry Reviews*, 18 (1976) 327–352. Where nitrogen is the ligand, L, typical transition metals are nickel, palladium and platinum. A five-membered ring is formed with the nitrogen ligand having the formula

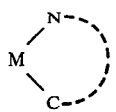

where the nitrogen ligand is sterically hindered and is typically tertiary. The ring structure is typically of the formulas

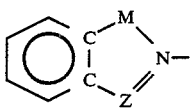 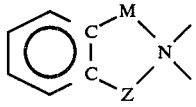

II   III where Z is nitrogen or carbon.

Where the ligand is phosphorus, the cyclic structure may have 4–6 members. Formula VII illustrates an example of a 4 membered cyclometallated complex having a phosphorus ligand.

VII

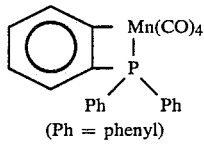

(Ph = phenyl)

Five-membered rings are formed preferentially, with the phosphorus ligand being sterically hindered. The five-membered ring typically has the formula shown below with the transition metal "M" being rhodium, palladium, platinum, cobalt and ruthenium.

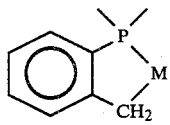

More particular examples of cyclometallated complexes having phosphorus ligands are shown in formulas VIII and IX.

VIII

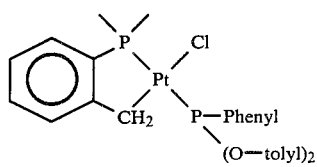

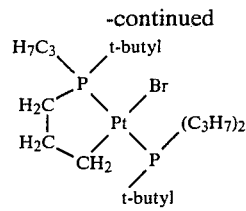

IX

Included within the cyclometallated complexes having phosphorus ligands are the phosphites.

These typically have a five-membered cyclic structure of the formula below.

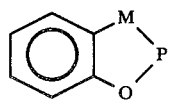

Examples of 5 membered cyclometallated transition metal complexes having a phosphite ligand are described with greater particularity by Dehand and Pfeffer in Table 4 of that reference on page 342, which include:

X

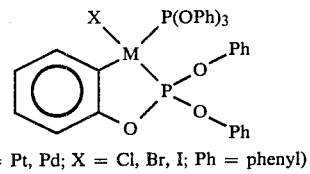

(M = Pt, Pd; X = Cl, Br, I; Ph = phenyl)

XI

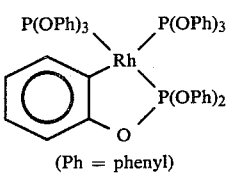

(Ph = phenyl)

Formula XII illustrates an example of a cyclometallated complex having a phosphorous ligand with a 6 membered ring structure:

XII

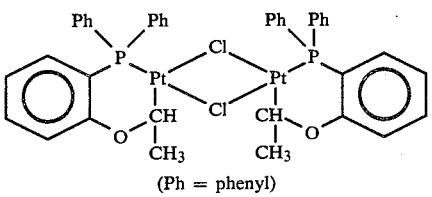

(Ph = phenyl)

Other suitable cyclometallated transition metal complexes with phosphite ligands are shown in formulas XIII–XVI where Ph=phenyl.

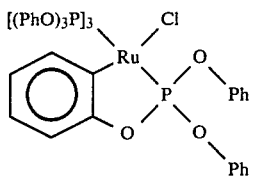

XIII

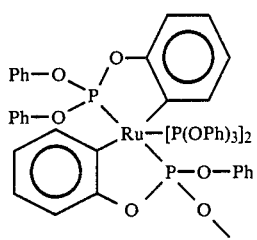

XIV

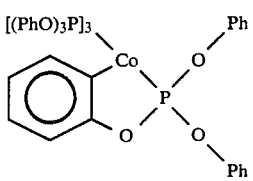

XV

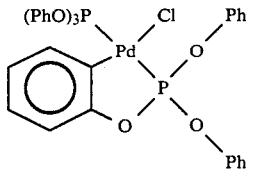

XVI and the ruthenium complex of formula XVII, which is a new composition of matter.

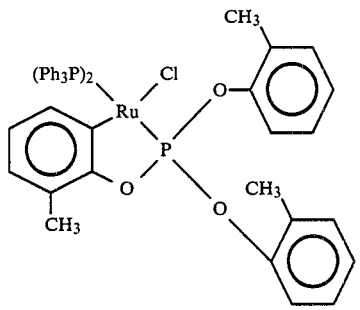

XVII

Cyclometallated complexes having arsenic, oxygen and sulphur ligands provide 5 membered ring structures of the general structures below

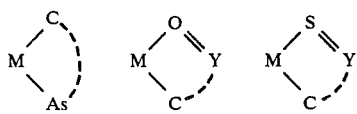

where Y is oxygen, sulphur or carbon. A particular cyclometallated complex with an arsenic ligand is shown in FIG. XVIII.

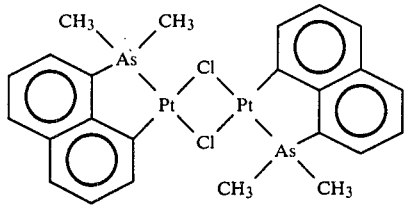

XVIII

Particular cyclometallated complexes having oxygen and sulphur ligands are shown in formulas XX and XXI.

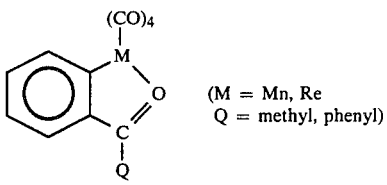

XX (M = Mn, Re
Q = methyl, phenyl)

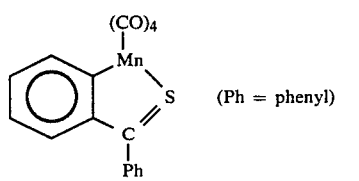

XXI (Ph = phenyl)

These cyclometallated catalysts have been found to be true homogeneous catalysts in accordance with the tests described by R. H. Crabtree et al in J.Amer.-Chem.Soc., 104 (1982) 107. These tests involve the reduction of nitrobenzene to anilene and distinguish the homogeneous catalysts from heterogeneous catalysts, such as colloidal metals.

In that the cyclometallated complexes operate as a homogeneous catalyst, they are dissolved within a solution during hydrogenation of the olefins and alkynes. The solutions are limited to inert solvents which dissolve the olefin and/or alkyne so as to permit exposure to the catalyst during reaction. Nonreactive solvents are required to maintain catalyst activity. The cyclometallated compounds retain their activity in most nonpolar organic solvents. Examples of suitable inert, nonpolar organic solvents include unsubstituted aromatic hydrocarbons, such as benzene, toluene and xylene. Aromatic nonpolar solvents are preferred. Unsubstituted aliphatic hydrocarbons are sufficiently inert; however, the olefins are not very soluble in most of these solutions. Polar solvents may be sufficiently inert where the polar group is not a hydroxy radical. Certain halogenated hydrocarbons may be too reactive, such as chloroform; while others are sufficiently inert under mild reaction conditions, such as methylene chloride. Other polar solvents which may be sufficiently inert are selected ketones, such as acetone. Mixtures of inert organic solvents are also suitable. The organic solvents which are preferred depend on the olefins and/or alkynes to be hydrogenated. Those inert organic solvents having a boiling point distinct from the reaction product are most preferred with toluene being preferred most often.

The catalysts retain their activity over a wide temperature range. The hydrogenation reaction preferably proceeds at a temperature within the range of about 20° C. to 220° C. Although higher and lower temperatures can be utilized, product yields are reduced due to either low reactivity at low temperatures or degradation of the hydrogenation product at high temperatures. The lower limit for the temperature is the minimum temperature at which the catalyst and olefin remain active. For a given catalyst, different temperatures may be necessary when hydrogenating different olefins or alkynes. The upper limit is the temperature at which the cyclometallated complex degrades. The most preferred reaction temperatures fall within the range of about 100° to 200° C.

The quantity of catalyst which is preferred falls within the range of 0.01 to 1.0 mole percent of the active ingredients, with a range of about 0.05 to 0.3 mole percent being most preferred. The actual metal concentration within the reaction mixture is preferably in the order of about 0.005 to 0.03% by weight active ingredients.

An embodiment of this invention is directed to a new composition of matter having the formula XVII shown above. This catalyst was formed by reacting $RuHCl(PPh_3)_3$ and excess tri-ortho-tolyl-phosphite. This reaction typically takes place in an organic solution, such as hexane, heptane and the like under a nitrogen blanket at a temperature in the range of about 60°–100° C. The product yield is purified by extraction with heptane and recrystallization from toluene/hexane mixtures.

The unsaturated hydrocarbon species which can be reacted include aliphatic and cyclic olefins and alkynes of from 2 to 10 carbon atoms. Hydrogenation of larger aliphatic and cyclic olefins and alkynes may be accomplished where the carbon unsaturation falls within the terminal portions of the hydrocarbon chain. Aromatic hydrocarbons of 8–18 carbon atoms having olefin or alkyne functionality can also be hydrogenated at the olefin or alkyne moieties. The ring structure of the aromatic hydrocarbon remains intact after hydrogenation, only the olefin or alkyne moieties are hydrogenated. Olefin and alkyne moieties on siloxanes of 1 to 10 —(Si—O)— units may be hydrogenated by the process comprising this invention. The siloxane polymer backbone remains intact after hydrogenation, with only the olefin or alkyne moieties being hydrogenated. The olefin and alkyne moieties on the aromatic hydrocarbons and the siloxanes are preferably radicals of from 2 to 4 carbon atoms. Where the radical has more than 4 carbon atoms, hydrogenation of olefin or alkyne functionality which is not on the terminal portions of the radical may be difficult due to steric effects. Hydrocarbons with acidic groups, such as carboxyl groups, will inactivate the cyclometallated complex so as to provide little or no hydrogenation. However, unsaturated hydrocarbons which contain non-acidic functional groups are suitable for use in this invention. For example, esters of the formula below are suitable

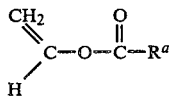

where $R^a$ is a hydrocarbon radical of from 1 to 8 carbon atoms.

The unsaturated hydrocarbons preferably comprise less than about 50 mole percent of the reaction mixture so as to enhance the percentage converted to saturated hydrocarbons. At very high concentrations, the unsaturated hydrocarbon may flood the cyclometallated catalysts and a portion may escape the reaction medium without hydrogenating. Typical olefins which can be hydrogenated include ethylene, propylene, butylene, pentene, hexene, heptene, cyclo-hexene, styrene, divinyl-tetramethyldisiloxane, and the like. Typical alkynes which can be hydrogenated include ethyne, propyne, butyne, pentyne, hexyne, and the like.

The quantity of hydrogen utilized in the reaction mixture is preferably at a value which will hydrogenate all of the olefins or alkynes within the reaction medium. However, any quantity of hydrogen will provide reaction in the presence of a cyclometallated catalyst. It is most preferable to utilize a slightly excessive quantity of hydrogen, such as about 2 to 2.5 moles per mole of unsaturated hydrocarbon linkages.

The order in which the reactants, hydrogen and the unsaturated hydrocarbon, are exposed to the cyclometallated catalyst is critical. Where hydrogen is the initial reactant introduced into the reaction medium containing the catalyst, hydrogenation of the subsequently introduced unsaturated hydrocarbon is very low and often eliminated. It is believed that the addition of hydrogen prior to the addition of the unsaturated hydrocarbon inactivates the catalyst by opening the ring structure. Without the cyclometallated ring structure, the catalytic activity of many transition metals is lost. For example, where the transition metal is cobalt, no reaction takes place except within cyclic complexes. In addition, palladium complexes do not provide catalysis unless in cyclic form. Where the transition metal exhibits catalytic activity in non-cyclometallated form, such as ruthenium, the cyclometallated form shows higher activity at room temperature and improved resistance to oxidative degradation. Where the order of addition is reversed, i.e. the olefin is introduced initially followed by hydrogen addition, the ring structure remains intact and complete hydrogenation of the olefin is expected under preferred conditions.

Although the cyclometallated catalysts show excellent resistance to degradation from exposure to moisture and air, it is preferable to perform the reaction over an inert atmosphere such as nitrogen or argon. The reaction solution need not be dried prior to use, but such a practice may be desirable for certain embodiments of this invention.

Conventional pressurized reactors are suitable for use in this invention. The hydrogenation reaction is typically performed in a batchwise fashion. The cyclometallated catalysts will provide activity following hydrogenation of the initial batch of unsaturated hydrocarbon. The addition of more unsaturated hydrocarbon and hydrogen to a reaction medium at a suitable temperature will provide further hydrogenation. The cyclometallated catalyst can be expected to provide over 300 batch cycles or turnovers without a significant loss in activity.

The following examples are provided to illustrate embodiments of this invention and are not intended to limit the scope of this invention to their contents.

EXAMPLE 1

Toluene (15 ml) and a ruthenium catalyst of Formula XIII (0.116 grams, 0.084 mmol) were combined in a 250 milliliter thickwalled glass bottle. The bottle was degassed with nitrogen and then pressurized with ethylene (50 psi, 33 mmol) and then hydrogen (50 psi, 33 mmol). The bottle was heated with stirring to 180° C.

for 4 hours. After cooling to room temperature, the gas above the solution was analyzed by infrared spectroscopy, which showed ethane was produced quantitatively, i.e. greater than 90% ethane present.

The solution from this reaction remained in the 250 ml thickwalled glass bottle and was recharged with ethylene (50 psi, 33 mmol) and hydrogen (60 psi, 39 mmol). The bottle was heated with stirring to 205° C. for 5 hours. The bottle was cooled to room temperature and a pressure of about 60 psi. Analysis of the gases by infrared spectrometry showed greater than 90% ethane present in the recovered gas. The reaction solution was then recovered from the bottle and filtered through 0.5 micron filter; the solution was found to be golden yellow at this point. The solution was then placed in a 90 ml bottle and charged with ethylene (50 psi, 10 mmol) and hydrogen (50 psi, 10 mmol). The bottle was heated with stirring for 6 hours at 170° C. The gases recovered from solution were analyzed by infrared spectrometry and showed to contain greater than 90% ethane.

EXAMPLE 2

This example illustrates the synthesis and utility of the cyclometallated complex of formula XVII. Hexane (30 ml), the complex RuHCl(PPh$_3$)$_3$ (1.05 g, 1.08 mmol), where Ph=phenyl, and excess tri-ortho-tolyl phosphite (3.5 ml, 11 mmol) were combined in a 250 ml round bottom flask. The solution was degassed with N$_2$ and refluxed for 30 minutes. The solution was filtered to recover an orange solid. The solid was purified by extraction with heptane and recrystallized from toluene/hexane. The ruthenium complex of formula XVII was obtained in 50% yield as an orange solid, having a melting point of 165° C. (decomp). Elemental analysis indicated C=67.24, H=4.94, P=8.95 and Ru=9.91. Calculated values were C=67.62, H=4.94, P=9.19 and Ru=9.99. Proton NMR in CDCl$_3$ gave peaks at 7.75, 6.67, 6.14, 1.88 and 1.68 PPM. Phosphorus NMR in CDCl$_3$ gave peaks at 167.71 (t,J=45 Hz) and 41.80 (d,J=45 Hz).

Toluene (10 ml) and a cyclometallated catalyst of formula XVII (0.088 g, 0.087 mmol) were placed in a 90 ml thickwalled glass bottle. The bottle was degassed with nitrogen and charged with ethylene (50 psi, 11 mmol) and then hydrogen (50 psi, 11 mmol). The contents of the bottle were stirred for 8 hours at 25° C. The gas above the solution was analyzed by infrared spectroscopy which showed ethane was produced quantitatively. The cyclometallated catalyst of formula XVII was recovered from the solution with no evidence of change.

CONTROL

Toluene (50 ml) was placed in a 90 ml thickwalled glass bottle. The bottle was degassed with nitrogen and then charged with ethylene (50 psi, 11.8 mmol) and then hydrogen (50 psi, 12 mmol). The bottle was heated with stirring to 190° C. for 4½ hours. The bottle was cooled to room temperature and a pressure of 80 psi. The gases were analyzed by infrared spectroscopy and found to contain only ethylene. No evidence of hydrogenation having occurred within the bottle was present.

HYDROGEN AS INITIAL REACTANT

Toluene (5 ml) and a cyclometallated catalyst of formula XIII (0.0187 gms, 0.0136 mmol) were added to a 90 ml thickwalled glass bottle. The bottle was degassed with nitrogen and then charged first with hydrogen (50 psi, 11.8 mmol) and then ethylene (50 psi, 11.8 mmol). The bottle was heated to 180° C. with stirring for 2 hours. The reaction was cooled and the gases were analyzed by infrared spectroscopy. Infrared analysis indicated that hydrogenation within the glass bottle of the ethylene was slight in that the gases comprised mostly ethylene.

COMPARATIVE EXAMPLE

This example illustrates hydrogenation of olefins utilizing a catalyst with no cyclometallated ring structure. The catalyst utilized was RuHCl(PPh$_3$)$_3$, with Ph=phenyl.

To 10 ml of toluene were added 0.102 grams (0.11 mmol) of the non-cyclometallated catalyst described above. The solution was maintained in a 90 ml thickwalled glass bottle, which was degassed with nitrogen and then charged with ethylene (45 psi, 8.9 mmol) and hydrogen (45 psi, 8.9 mmol). The bottle was stirred at room temperature for 2 hours until a pressure of 45 psi was obtained. Analysis of the gases by infrared spectrometry showed a 50—50 mixture of ethylene:ethane. Proton NMR suggested degradation of the catalyst occurred. Repressurizing with H$_2$ and ethylene resulted in no further hydrogenation.

This is a significant contrast from the results obtained from the cyclometallated species of formula XVII, which did not degrade and provided a higher degree of conversion.

EXAMPLE 3

Toluene (5 ml) and a cyclometallated complex of formula XVII (0.011 gms, 0.011 mmol) were combined in a 90 ml thick walled glass bottle. Styrene (1 ml, 8.75 mmol) was added to the solution and the bottle was sealed. The bottle was then pressurized with hydrogen (80 psi) and heated to 165° with stirring for 3½ hours. After cooling, the solution was analyzed by gas chromatography, which showed a 96% conversion to ethyl benzene.

EXAMPLE 4

Toluene (5 ml) and a cyclometallated complex of formula XVII (0.13 gms, 0.13 mmol) were combined in a 90 ml thick walled glass bottle. Vinyl acetate (1 ml, 0.011 mol) was added to this solution and the bottle was sealed, pressurized with hydrogen (80 psi, 19 mmol) and heated to 170° C. for 2 hours with stirring. After cooling, gas chromatograph analysis showed 20% conversion to ethyl acetate.

COMPARATIVE EXAMPLE

Toluene (5 ml) and a noncyclometallated catalyst of the formula ClRh(PPh$_3$)$_3$, where Ph=phenyl, (0.0174 grams, 0.019 mmol) were combined in a 90 ml thick walled glass bottle. The vinyl acetate (1 ml, 0.011 mol) was added to the solution and the bottle was sealed, pressurized with hydrogen (80 psi, 19 mmol) and heated to 160° C. for 2 hours with stirring. After cooling, gas chromatograph analysis showed 13% conversion to ethyl acetate.

EXAMPLE 5

Toluene (5 ml) and a cyclometallated complex of formula XVII (0.0369, 0.030 mmol) were combined in a 90 ml thick walled glass bottle. Cyclohexene (1 ml, 9.9 ml) was added to the solution and the bottle was sealed, pressurized with hydrogen (50 psi, 11.7 mmol) and heated to 130° for 5 hours with stirring. After cooling, gas chromatograph analysis showed that 100% conversion to cyclohexane had occurred.

The ability of the complex to catalyze the hydrogenation of nitrobenzene to analine has been shown by Crabtree et al, in the reference cited above, to be an operational test for the presence of metal colloids. Failure to catalyze this reaction is good evidence that the catalyst is truly homogeneous.

Nitrobenzene (1 ml) was added to the catalyst solution described above. The solution was pressurized with hydrogen (50 psi) and heated to 120° C. for 4 hours with stirring. After cooling, gas chromatograph analysis showed only a trace (less than 3%) of aniline, which is consistent with the cyclometallated catalyst of formula XVII being truly homogeneous.

COMPARATIVE EXAMPLE

The complex ClRh(PPh$_3$)$_3$, wherein Ph is phenyl, (0.033 gms, 0.036 mmol) was combined with toluene (5 ml) and cyclohexene (1 ml, 9.9 mmol). The complex described above was a noncyclometallated species. The bottle was sealed, pressurized with hydrogen (50 psi, 11.7 mmol) and heated to 130° C. for 5 hours with stirring. Gas chromatograph analysis showed 80% conversion to cyclohexane had occurred.

This catalyst was analyzed to determine whether it is truly homogeneous. Nitrobenzene (1 ml) was added to the above solution within a 90 ml thick walled glass bottle. The bottle was pressurized with hydrogen (50 psi) and heated to 110° C. for 45 minutes with stirring. After cooling, gas chromatograph analysis showed 29% conversion to aniline. These results are consistent with a portion of the catalysts being an active rhodium colloid within the solution. Therefore, the complex ClRh(PPh$_3$)$_3$, where Ph is phenyl, is not a truly homogeneous catalyst under these conditions.

EXAMPLE 6

Toluene (5 ml) and a cyclometallated complex of formula XVII (0.0339, 0.032 ml) were combined in a 90 ml thick walled glass bottle. To this solution were added 4.4 ml (1 ml) of 1,3-divinyl-tetramethyldisiloxane. The bottle was then sealed, pressurized with hydrogen (45 psi, 10.6 mmol) and heated to 120° C. for 3 hours with stirring. After cooling, gas chromatograph analysis showed the following materials present: 1,3-divinyl-tetramethyl-disiloxane (10.3%), 1-ethyl, 3-vinyl-tetramethyldisiloxane (20.8%) and 1,3-diethyl-tetramethyl-disiloxane (68.9%). The identity of the latter two products was confirmed by GCMS analysis.

EXAMPLE 7

Toluene (5 ml) and a cyclometallated complex catalyst of formula XVII (0.010 gms, 1.0199 mmol) were combined in a 90 ml thick walled glass bottle. To this bottle were added 5.1 mmol (0.5 ml) of 1 pentyne. The bottle was sealed, pressurized with hydrogen (50 psi, 11.7 ml) and stirred at room temperature for 48 hours. Gas chromatograph analysis at this point showed 10% conversion to a 1:1 mixture of 1-pentene and n-pentane had occurred. The contents of the bottle were repressurized with hydrogen (50 psi) and heated to 110° C. for 17 hours with stirring. After cooling, gas chromatograph analysis showed a complete conversion to a mixture of about 1:1 n-pentane and pentenes (a mixture of 1-pentene (67%) and 2-pentene (33%)). This solution was once again repressurized with hydrogen (50 psi) and heated to 155° C. for 4 hours with stirring. Gas chromatograph analysis showed that 1 pentene was selectively hydrogenated to n-pentane.

EXAMPLE 8

To a 250 ml thickwalled glass bottle were added 1-hexene (4 ml, 32.9 mmol) and a catalyst of formula XIII (0.051 gms, 0.37 mmol). The bottle was degassed with nitrogen, charged with hydrogen (100 psi, 69.5 mmol), heated to 156° C. and stirred for 15 hours. The bottle was then cooled to room temperature and a pressure of 55 psi. The contents were recovered and analyzed by gas chromatograph analysis and GCMS which showed that n-hexane was produced in 100% yield.

EXAMPLE 9

Toluene (15 ml) and a noncyclometallated catalyst of the formula CoH[P(OPh)$_3$]$_4$ (0.09 gms, 0.075 mmol), with Ph=phenyl, were placed in a 90 ml thickwalled glass bottle. The bottle was degassed with nitrogen and then charged with ethylene (50 psi, 10 mmol) and hydrogen (50 psi, 10 mmol). The bottle was heated with stirring to 210° C. for 5 hours. The solution was colorless and a dark precipitate formed within the solution. The gases were analyzed by infrared spectrometry and found to contain 100% ethylene.

To 10 ml of toluene were added a cobalt cyclometallated catalyst of formula XV (0.087 gms, 0.067 mmol). The solution was placed in a 90 ml glass bottle and degassed with nitrogen. The bottle was then charged with ethylene (50 psi, 11 mmol) and hydrogen (50 psi, 11 mmol). The bottle was heated with stirring at 207° C. for 4 hours. Analysis of the gases by infrared spectrometry showed greater than 90% ethane.

The hydrogenation of 1-hexene was carried out in the presence of 0.116 gms (8.9 mmol) of the cyclometallated catalyst of formula XV. A solution of 10 ml of benzene was placed in a 90 ml thickwalled glass bottle which was charged with hydrogen (80 psi, 18 mmol) and heated with stirring to 85° C. for three hours. The quantity of hexene was utilized was 1 milliliter (7.9 mmol). After reaction, the bottle was cooled to room temperature and vented. The solution was analyzed by gas chromatography which showed n-hexane with no hexene present. The solution was filtered and returned to the 90 ml glass bottle and recharged with a similar quantity of hexene and hydrogen. The bottle was stirred with heating for 4½ hours at 190° C. The solution was found to contain n-hexane with no hexene present.

EXAMPLE 10

To 10 ml of toluene were added 0.06 gms of a noncyclometallated catalyst having the formula PdCl$_2$[P(OPh)$_3$]$_2$ (0.083 mmol). The solution was placed within a 90 ml thickwalled glass bottle which was degassed with nitrogen and charged with ethylene (50 psi, 11 mmol) and hydrogen (50 psi, 11 mmol). The bottle was heated with stirring to 192° C. for 6 hours. A palladium mirror formed in the bottle and analysis of the gases showed that only ethylene was present.

A palladium cyclometallated catalyst having the formula XVI (0.069 gms, 0.091 mmol) was added with 10 ml toluene in a glove box and placed in a 90 ml glass bottle. The bottle was charged with ethylene (50 psi, 11 mmol) and hydrogen (50 psi, 11 mmol) and then heated to 192° C. for four hours. After the reaction, a dark precipitate was present. The gases were analyzed by infrared spectrometry and shown to contain greater than 90% ethane. The solution was taken into the glove box and filtered through a 0.5 micron filter. The filtrate was returned to a 90 ml glass bottle which was recharged with 1-hexene (0.9 ml, 7 mmol) and hydrogen (100 psi, 24 mmol). The bottle was heated with stirring at 180° C. for eight hours. The solution was analyzed by gas chromatography and found to contain n-hexane with no hexene present.

Although the above examples have shown various modifications of the present invention, further modifications are possible by one skilled in the art without departing from the scope and spirit of this invention.

What is claimed is:

1. A method for hydrogenating unsaturated hydrocarbons comprising: reacting hydrogen, in a solution of a cyclometallated catalyst at a temperature above about 20° C., with an unsaturated hydrocarbon selected from the group consisting of aliphatic and cyclic olefins and alkynes of from 2 to 10 carbon atoms, aromatic hydrocarbons of from 8 to 18 carbon atoms having olefinic or alkyne functionality within hydrocarbon radicals of from 2 to 4 carbon atoms and siloxanes of from 1 to 10 —(Si—O)— units having olefinic or alkyne functionality within hydrocarbon radicals of from 2 to 4 carbon atoms, subject to the proviso that said unsaturated hydrocarbons contain no acidic functional groups, said unsaturated hydrocarbon comprising less than about 50 mole percent of the reaction mixture and said cyclometallated catalyst having a 4 to 6 membered ring structure with a chemically combined unit of the formula

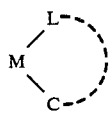

wherein M is a transition metal, L is a ligand selected from the group consisting of phosphorous, nitrogen, arsenic, oxygen and sulfur and C is a covalently bonded carbon atom of a hydrocarbon species having at least 6 carbon atoms.

2. A method as in claim 1 wherein the temperature is selected from the range of about 100° to 200° C.

3. A method as in claim 1 wherein the quantity of unsaturated hydrocarbon falls within the range of about 5 to 20 mole percent of said reaction medium.

4. A method as in claim 1 wherein the unsaturated hydrocarbon is an olefin selected from the group consisting of ethylene, propylene, butylene, pentene, hexene, heptene, styrene, cyclo-hexene and divinyl-tetramethyl-disiloxane.

5. A method as in claim 1 wherein the unsaturated hydrocarbon is an alkyne selected from the group consisting of ethyne, propyne, butyne, pentyne, hexyne and heptyne.

6. A method as in claim 1 wherein the transition metal is selected from the group consisting of palladium, platinum, cobalt, ruthenium, platinum, molybdenum and manganese.

7. A method as in claim 5 wherein the ligand L is phosphorous and the ring structure within the cyclometallated catalysts is of the formula:

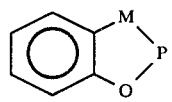

8. A method as in claim 1 wherein the catalyst is selected from the group consisting of

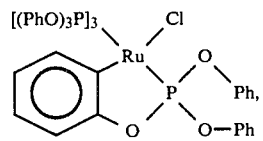

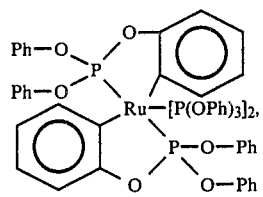

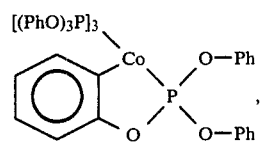

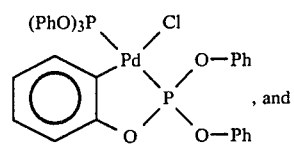

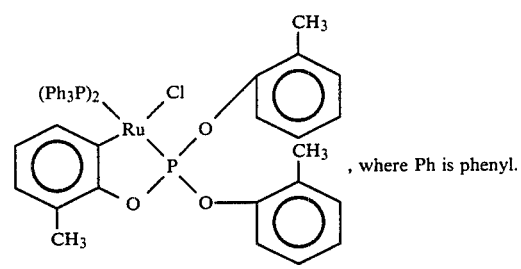

, where Ph is phenyl.

9. A method as in claim 1 wherein the solvent is selected from the group consisting of toluene, benzene and xylene.

10. A method as in claim 1 wherein the solution of cyclometallated catalyst contains about 0.01 to 1 mole percent cyclometallated complex based on said unsaturated hydrocarbon.

11. A method for hydrogenating unsaturated hydrocarbons comprising reacting an unsaturated hydrocarbon with hydrogen in a solution of cyclometallated transition metal complex catalysts at a temperature within the range of about 20° to 200° C., said cyclometallated transition metal complex catalysts being selected from the group consisting of

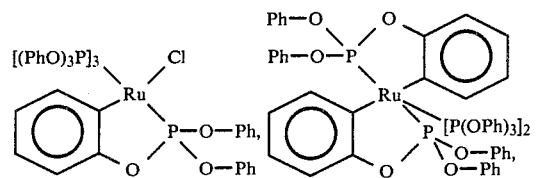

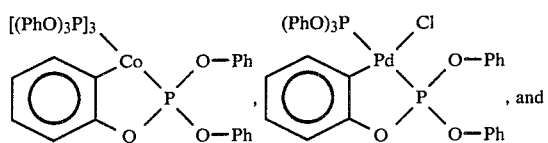

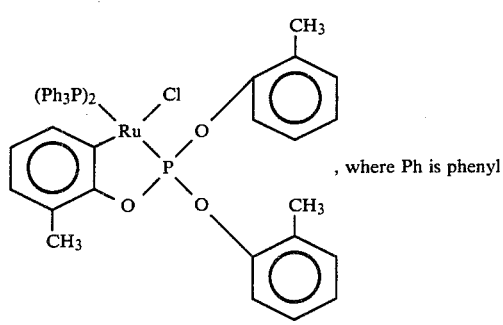

, where Ph is phenyl said solution being selected from the group consisting of toluene, benzene, and xylene;

said olefin being selected from the group consisting of ethylene, pentyne, hexene, cyclo-hexene, heptene, styrene and divinyl tetramethyl-disiloxane; and said olefin comprising less than about 50 mole % of said reaction mixture.

12. A method as in claim 11 wherein the quantity of cyclometallated transition metal complex catalysts falls within the range of 0.01 to 1 mole percent based on said unsaturated hydrocarbon.

13. A method as in claim 12 wherein the reaction takes place under an inert atmosphere.

14. A cyclometallated ruthenium complex of the formula

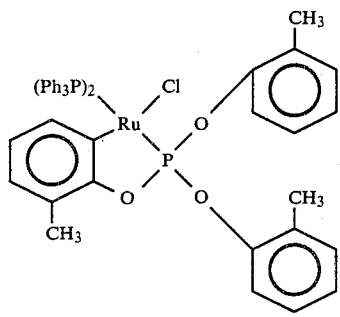

* * * * *